United States Patent [19]

Gapinski

[11] Patent Number: 4,801,616

[45] Date of Patent: Jan. 31, 1989

[54] DIPHENYLMETHANONE COMPOUNDS AND ANTI-INFLAMMATORY USE THEREOF

[75] Inventor: D. Mark Gapinski, Indianapolis, Ind.

[73] Assignee: Eli Lilly and Company, Indianapolis, Ind.

[21] Appl. No.: 843,907

[22] Filed: Mar. 25, 1986

[51] Int. Cl.$^4$ .................. A61K 31/41; A61K 31/275; C07D 257/02; C07C 121/76
[52] U.S. Cl. .................................... 514/381; 514/520; 514/545; 514/546; 514/571; 514/621; 514/687; 558/389; 560/52; 560/140; 562/459; 564/169; 568/332; 568/333
[58] Field of Search ............... 548/253; 514/381, 520, 514/545, 546, 571, 621, 687; 558/389; 560/52, 140; 562/459; 564/169; 568/332, 333

[56] References Cited

U.S. PATENT DOCUMENTS

| | | | |
|---|---|---|---|
| 2,962,533 | 11/1960 | Hardy et al. | 558/389 |
| 3,600,437 | 8/1971 | Marshall | 548/253 |
| 3,649,637 | 3/1972 | Howes et al. | 548/253 |
| 4,058,559 | 11/1977 | Jones et al. | 548/253 |
| 4,281,008 | 7/1981 | Chamberlain et al. | 424/269 |
| 4,424,231 | 1/1984 | Bankwick et al. | 424/274 |

FOREIGN PATENT DOCUMENTS

| | | |
|---|---|---|
| 28063 | 5/1981 | European Pat. Off. . |
| 108592 | 5/1984 | European Pat. Off. . |
| 132366 | 1/1985 | European Pat. Off. . |
| 132367 | 1/1985 | European Pat. Off. . |
| 1415295 | 11/1975 | United Kingdom . |

*Primary Examiner*—David B. Springer
*Attorney, Agent, or Firm*—Edward P. Gray; Leroy Whitaker

[57] ABSTRACT

This invention provides certain diphenylmethane derivatives, their pharmaceutical formulations, and their use in treating inflammation and arthritis in mammals.

18 Claims, No Drawings

DIPHENYLMETHANONE COMPOUNDS AND ANTI-INFLAMMATORY USE THEREOF

BACKGROUND OF THE INVENTION

Mammals, both humans and animals, are known to suffer from various conditions involving inflammation with concomitant swelling, tenderness, decreased mobility, pain, and fever. While a number of antiinflammatory agents are effective in the symptomatic treatment of such inflammatory conditions as rheumatoid arthritis, rheumatoid spondylitis, osteoarthritis, degenerative joint diseases, and the like, many such agents have a number of undesirable side effects, such as gastric irritation and the like.

The etiology and pathogenesis of rheumatic and arthritic diseases remain obscure. Meanwhile, the need continues for safer, better calibrated drugs which will slow the process and alleviate the symptoms of inflammatory diseases. For example, in rheumatoid arthritis, any agent which reduces the inflammation is important in lessening or delaying the development of crippling.

SUMMARY OF THE INVENTION

This invention provides diphenylmethane compounds of the formula

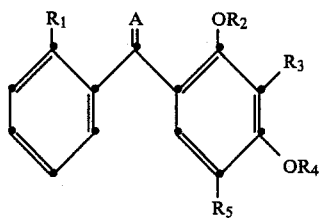

and pharmaceutically acceptable salts thereof wherein
$R_1$ is —OH, —O—($C_1$–$C_4$ alkyl), halo, or —OCO($C_1$–$C_4$ alkyl);
A is O, $CH_2$, or CH($C_1$–$C_4$ alkyl);
$R_2$ is hydrogen or $C_1$–$C_4$ alkyl;
$R_3$ is $C_1$–$C_4$ alkyl or $C_2$–$C_4$ alkenyl;
$R_4$ is —H, $C_1$–$C_4$ alkyl, —CO($C_1$–$C_4$ alkyl), -alk-$R_6$, or

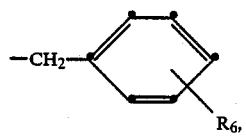

or $R_3$ and $R_4$ when taken with the oxygen atom to which $R_4$ is attached are —$CH_2CH(CH_3)O$—;
$R_5$ is —H or $C_1$–$C_4$ alkyl; and
$R_6$ is —CN, —COOH, —COO($C_1$–$C_4$ alkyl), —$CONR_7R_8$, or

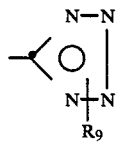

where
$R_7$ and $R_8$ are each independently hydrogen or $C_1$–$C_3$ alkyl,
$R_9$ is hydrogen or $C_1$–$C_4$ alkyl, and "alk" is a divalent organic radical derived from a $C_1$–$C_8$ aliphatic hydrocarbon.

This invention also provides a method of treating inflammation and arthritis in a mammal in need of such treatment which comprises administering to said mammal a therapeutically effective amount of a compound of this invention.

According to a further aspect of the present invention there is provided a pharmaceutical formulation which comprises as active ingredient a compound of formula I as defined above associated with a pharmaceutically acceptable carrier therefor.

DETAILED DESCRIPTION AND PREFERRED EMBODIMENTS

The preferred compounds of this invention are those of the above formula wherein
(a) $R_5$ is hydrogen,
(b) A is O,
(c) $R_1$ is hydroxy or methoxy,
(d) $R_2$ is hydrogen or methyl,
(e) $R_3$ is $C_1$–$C_4$ alkyl, especially propyl, and
(f) $R_4$ is -alk-$R_6$, especially where $R_6$ is unsubstituted 5-tetrazolyl.

The term "$C_1$–$C_4$ alkyl" refers to straight and branched aliphatic radicals of 1 to 4 carbon atoms such as methyl, ethyl, propyl, isopropyl, butyl, isobutyl, sec-butyl, and tert-butyl, and includes within its definition the term "$C_1$–$C_3$ alkyl".

The term "$C_2$–$C_4$ alkenyl" refers to straight and branched radicals with 2 to 4 carbon atoms such as ethenyl, allyl, isopropenyl, butenyl, isobutenyl, and the like.

The term "alk" refers to a divalent organic radical derived from a straight or branched $C_1$–$C_3$ aliphatic hydrocarbon and is preferably di—, tri-, or tetra-methylene. The term "halo" refers to chloro, bromo, or iodo.

The invention includes the pharmaceutically acceptable base addition salts of compounds wherein $R_6$ is —COOH or 5-tetrazolyl. Such salts may be derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include sodium hydroxide, sodium acetate, ammonium hydroxide, potassium carbonate, sodium bicarbonate, calcium hydroxide, methylamine, diethylamine, ethylenediamine, cyclohexylamine, ethanolamine, and the like. The potassium and sodium salt forms are particularly preferred.

The compounds of this invention may be made by methods known in the art. For example, many of the compounds may be prepared according to the processes of Scheme I.

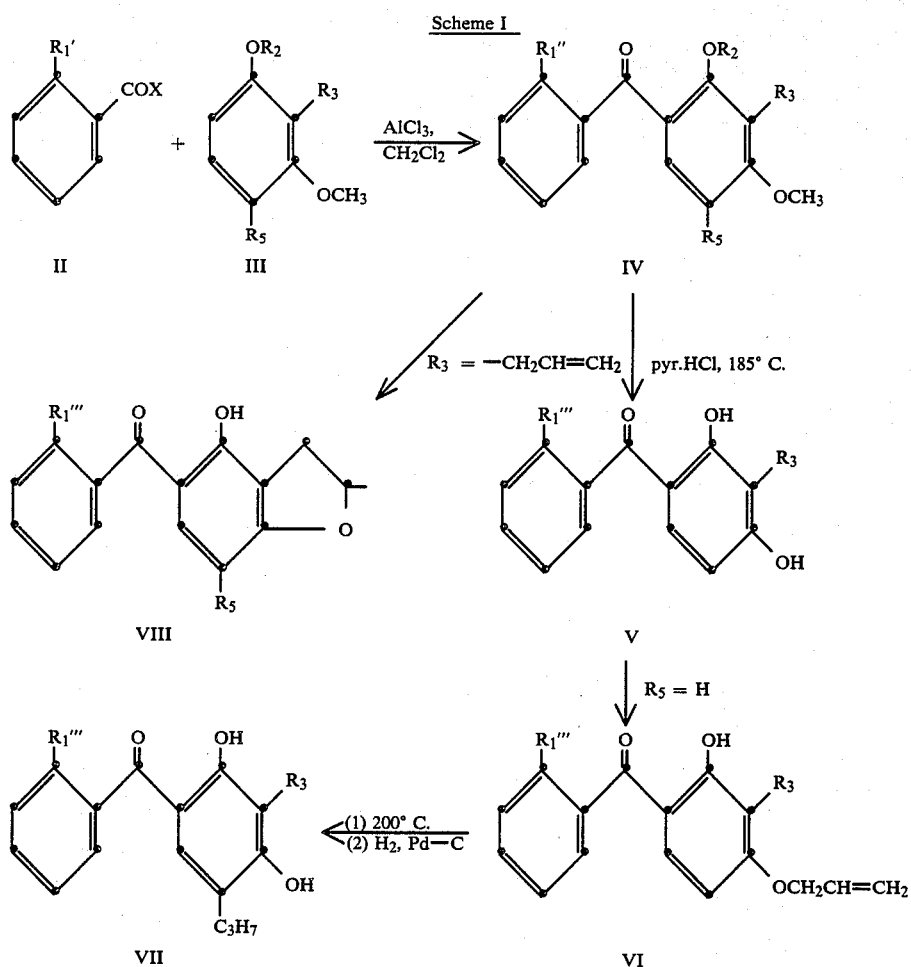

Scheme I wherein X is bromo or chloro, $R_1'$ is $C_1-C_4$ alkoxy or halo, $R_1''$ is hydroxy, $C_1-C_4$ alkoxy, or halo, and $R_1'''$ is hydroxy or halo.

Following Scheme I, a dialkoxybenzene (III) is acylated with acid chloride or bromide II to provide the corresponding benzophenone IV. Standard Friedel-Crafts acylating conditions are employed. Generally, three equivalents of aluminum chloride are employed with equimolar amounts of II and III in a non-reactive solvent such as methylene chloride at temperatures from about 0°–30° C. However, other Lewis acids, such as zinc chloride, may also be employed. The reaction provides a mixture of compounds wherein $R_2$ is both alkoxy and hydroxy. Moreover, when the acid halide II contains an alkoxy substituent, the reaction provides both the hydroxy and alkoxy derivatives as defined by $R_1''$. This mixture of products may be resolved by methods known in the art, such as fractional crystallization, chromatography, and the like. Alternatively, the mixture of products can be employed in subsequent transformations. For example, the alkoxy substituent(s) may be transformed into the corresponding hydroxy group(s) upon treatment with molten pyridine hydrochloride at 180°–190° C. This procedure dealkylates all alkoxy groups. The resulting phenols may, in turn, be alkylated according to standard procedures known in the art. A preferred alkylating procedure involves the reaction of the phenol with a dialkyl sulfate in a nonreactive solvent such as methyl ethyl ketone, preferably in the presence of a base such as potassium carbonate. The 4-hydroxy group can be selectively alkylated to provide compounds wherein $R_4$ is alkoxy. Alternatively, the other phenol groups may be alkylated after the functionalization of the 4-hydroxy moiety.

Similarly, any or all of the phenol functionalities may be acylated according to standard methods known in the art. The preferred conditions for introducing acyl functionalities both as the $R_1$ and $R_4$ substituents involves the reaction of the corresponding phenol with the appropriate acyl anhydride in the presence of dimethylaminopyridine and a non-reactive base, such as triethylamine or pyridine, preferably in the presence of a non-reactive solvent, such as diethyl ether.

An alternate method of introducing a propyl group for $R_5$ involves the transformation of the phenol IV, where $R_5$ is hydrogen, to the allyl ether VI by treatment with an allyl halide, a non-reactive solvent such as methyl ethyl ketone, and an acid scavenger such as potassium carbonate under standard alkylation conditions. Heating the allyl ether VI at 200° C. rearranges the allyl group to a compound related to compound V wherein $R_5$ is allyl, which can then be reduced under standard conditions, such as catalytic hydrogenation, to provide the propyl derivative VII.

When R₃ is allyl, acidic demethylation of the methoxy group in IV with heating leads to ring closure and formation of the dihydrobenzofuran of formula VIII. Typically, this demethylation ring closure occurs upon heating with hydrobromic acid and acetic acid whereas heating with pyridine hydrochloride results in the dealkylated but noncyclized compounds V.

Phenols of the formula IX may be further transformed into other compounds of this invention as summarized in Scheme II.

are prepared by treating the tetrazoles of formula XIII with standard alkylating reagents, such as an alkyl iodide to provide both the 1H-and 2H-alkyltetrazole isomers.

As discussed earlier, any of the above compounds containing phenol functionality can be transformed into the corresponding alkoxy derivative by standard alkylation procedures. Moreover, alkoxy-containing compounds may be dealkylated to the corresponding phenol under a variety of conditions. Phenols may also be acylated and acyloxy-containing compounds may be hydrolyzed to the corresponding phenols. When $R_3$ is $C_2-C_4$

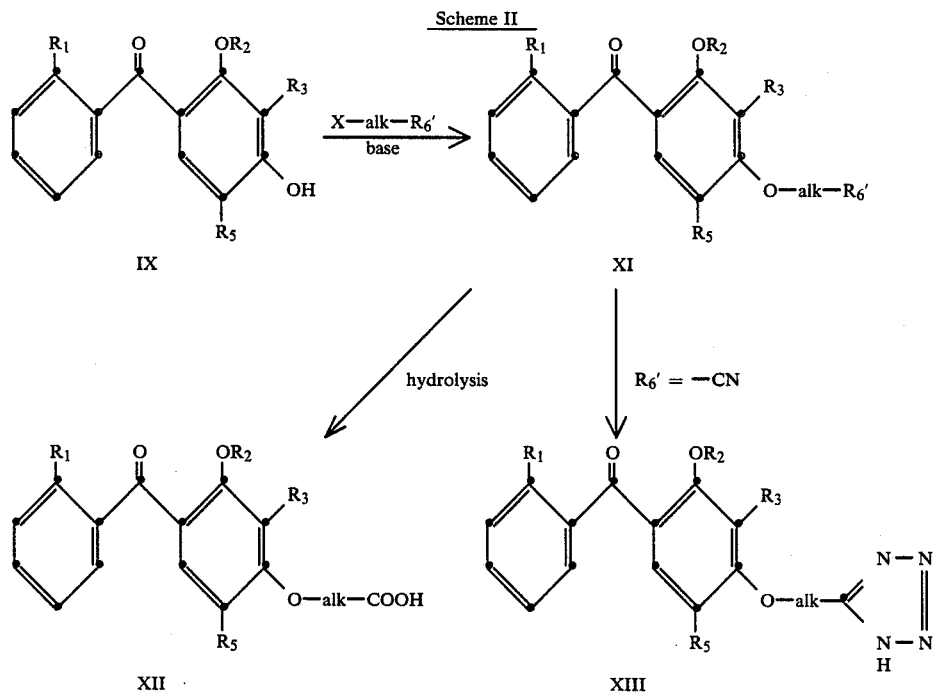

where $R_6'$ is —CN or —COO($C_1-C_4$ alkyl).

The transformation of IX into XI is a standard alkylation which is accomplished by allowing approximately equimolar amounts of IX and X-alk-$R_6'$ to react in the presence of an acid scavenger, such as potassium carbonate or sodium hydride, preferably in the presence of a non-reactive solvent such as methyl ethyl ketone or dimethylformamide. This reaction provides the ester and nitrile compounds of formula XI which can then be transformed into the acid derivatives (XII) upon basic hydrolysis, or, when $R_6'$ is cyano, converted into the tetrazole compound XIII upon treatment with an azide reagent, such as ammonium azide or tri n-butylstannyl azide in a non-reactive solvent, such as tetrahydrofuran, at temperatures from about 20° C. up to the reflux temperature of the reaction mixture. The carboxylic acid derivatives XII may be transformed into other esters by standard esterification techniques or transformed into the amide derivatives of this invention, usually upon transformation first to the corresponding acid chloride, such as after treatment with thionyl chloride at reflux conditions, followed by treatment of the acid chloride with corresponding amine HNR₇R₈ in a non-reactive solvent such as diethyl ether. The alkylated tetrazoles alkenyl, reduction to the corresponding $C_2-C_4$ alkyl functionality may be accomplished, for example, through catalytic hydrogenation. Finally, any of the benzophenone compounds as described above may be transformed into the corresponding ethenyl derivative (i.e., A is $CH_2$ or $CH(C_1-C_4$ alkyl)) under the appropriate Wittig conditions. It is preferred that the Wittig reaction be performed on the benzophenone compound before the introduction of any other reactive group, such as a tetrazole moiety. Typically, a slight molar excess of an ylid precursor, such as an alkyl triphenylphosphonium bromide, and a strong organic base, such as n-butyllithium in a non-reactive solvent such as tetrahydrofuran, are employed with the benzophenone. After the introduction of the ethene functionality, other derivatizations as previously described may be performed.

Intermediates II, III, and other required reagents are commercially available, are known in the literature, or can be prepared by methods known in the literature or by the methods described in the following examples.

Depending upon the definitions of R₃, R₄, and R₅, the compounds of formula I may exist in various isomeric forms. This invention is not limited to any particular isomer but includes all possible individual isomers and racemates.

The following examples further illustrate the preparation of the compounds of this invention. The examples are illustrative only and are not intended to limit the scope of the invention in any way.

EXAMPLES 1-3

(2,4-Dimethoxy-3-propylphenyl)(2-methoxyphenyl)methanone,
(2,4-dimethoxy-3-propylphenyl)(2-hydroxyphenyl)methanone, and
(2-hydroxy-4-methoxy-3-propylphenyl)(2-hydroxyphenyl)methanone To a slurry of 25 g of 1,3-dimethoxy-2-propylbenzene and 74 g of aluminum chloride in 1 liter of methylene chloride at 0° C. were added 23.7 g of 2-methoxybenzoyl chloride in dropwise fashion. The reaction was maintained at 0° C. for two hours and allowed to warm to room temperature. After stirring an additional hour, the reaction was poured into a slurry of dilute hydrochloric acid and ice. The layers were separated and the organic layer was washed 3 times with a sodium bicarbonate solution, followed by water, drying over magnesium sulfate, and evaporation in vacuo. The residue was purified by high pressure liquid chromatography over silica gel using a 5-25% ethyl acetate in hexane gradient. Fractions containing the trimethoxy and dimethoxy benzophenones were combined and concentrated to dryness to provide 9.0 g of the two benzophenones as a mixture. The mixture was subsequently used in the demethylation reaction of Example 4 which follows. A second experiment following the same procedure provided the following compounds in pure form:

1. (2,4-Dimethoxy-3-propylphenyl)(2-methoxyphenyl)methanone, 4% yield, oil.
    Analysis for $C_{19}H_{22}O_4$:
    Calc.: C, 72.59; H, 7.05;
    Found: C, 72.84; H, 6.89.
2. (2,4-Dimethoxy-3-propylphenyl)(2-hydroxyphenyl)methanone, 13% yield, oil.
    Analysis for $C_{18}H_{20}O_4$:
    Calc.: C, 71.98; H, 6.71;
    Found: C, 72.20; H, 6.87.
3. (2-Hydroxy-4-methoxy-3-propylphenyl)(2-hydroxyphenyl)methanone, was detected but not isolated. See Example 5 which follows for preparation by an alternate route.

EXAMPLE 4

(2,4-Dihydroxy-3-propylphenyl)(2hydroxyphenyl)methanone

Pyridine hydrochloride (39.7 g) was heated to 180° C. for 1 hour. To this molten salt were added 10.8 g of the unresolved mixture of products from Examples 1-3. The reaction mixture was stirred at 180° C. for 3 hours and then allowed to cool to approximately 25° C. The solid mass was dissolved in water and extracted 3 times with ethyl acetate. The combined organic extracts were washed with 1N hydrochloric acid, dried over magnesium sulfate, and evaporated to dryness. The residue was purified by high pressure liquid chromatography over silica gel eluting with a 5-15% (v/v) ethyl acetate/hexane gradient. The appropriate fractions were combined and evaporated in vacuo. Crystallization from hexane/ethyl acetate provided 2.33 g of the desired title product, m.p. 110°-113° C.
Analysis for $C_{16}H_{16}O_4$:
Calc.: C, 70.58; H, 5.92;
Found: C, 70.85; H, 5.79.

EXAMPLE 5

Alternate preparation of (2-hydroxy-4-methoxy-3-propylphenyl)(2-hydroxyphenyl)methanone To a stirred solution of three grams of (2,4-dihydroxy-3-propylphenyl)(2-hydroxyphenyl)methanone in 50 ml of 2-butanone were added 3.04 g of potassium carbonate and 0.52 ml of dimethyl sulfate. The mixture was stirred at reflux temperature overnight, cooled to 25° C., and poured into diethyl ether/water. The layers were separated. The organic layer was washed twice with water, once with a saturated sodium chloride solution, dried over magnesium sulfate, and concentrated providing 2.94 g of the desired title product as an oil.
Analysis for $C_{17}H_{18}O_4$:
Calc.: C, 71.31; H, 6.34;
Found: C, 71.11; H, 6.54.

EXAMPLE 6

[4-(Acetyloxy)-2-hydroxy-3-propylphenyl][2(acetyloxy)phenyl]methanone

Five grams of (2,4-dihydroxy-3-propylphenyl)-(2-hydroxyphenyl)methanone, 5.63 ml of triethylamine, and approximately 50 mg of dimethylaminopyridine were dissolved in 50 ml of diethyl ether at 0° C. Acetic anhydride (3.8 ml) was added dropwise. After stirring for 1 hour, the reaction mixture was partitioned between diethyl ether and water. The organic layer was separated, washed with 1N hydrochloric acid, a saturated solution of sodium bicarbonate, and a saturated solution of sodium chloride, dried over magnesium sulfate, and concentrated in vacuo. Purification by high pressure liquid chromatography over silica gel eluting with a 10-25% ethyl acetate in hexane gradient and concentration of the appropriate fractions provided 2.6 g of the desired title product as an oil.
Analysis for $C_{20}H_{20}O_6$:
Calc.: C, 67.41; H, 5.66;
Found: C, 68.41; H, 5.82.

EXAMPLE 7

(2,4-Dihydroxy-3,5-dipropylphenyl)(2-hydroxyphenyl)methanone

A. Preparation of (4-allyloxy-2-hydroxy-3-propylphenyl)(2-hydroxyphenyl)methanone.

A mixture of 8.72 g of (2,4-dihydroxy-3-propylphenyl)(2-hydroxyphenyl)methanone, 1.94 g of allyl bromide, 11.06 g of potassium carbonate, and a catalytic amount of potassium iodide in 100 ml of methyl ethyl ketone was stirred at reflux temperature for 3 hours. The reaction mixture was evaporated in vacuo, stirred with water/ethyl acetate, and the layers were separated. The organic layer was washed twice with water, once with a saturated sodium chloride solution, dried over magnesium sulfate, and evaporated in vacuo. The resulting oil was purified by high pressure liquid chromatography over silica gel eluting with a 5-25% ethylacetate in hexane gradient. The appropriate fractions were combined to provide 2.96 g of the desired subtitle intermediate which was used without further purification.

B. Preparation of (2,4-dihydroxy-3,5-dipropylphenyl)(2-hydroxyphenyl)methanone.

The allyloxy intermediate of Example 7A above (2.96 g) was heated to approximately 180° C. for 6 hours. After cooling, the residue was chromatographed over silica gel using a 0-10% ethyl acetate in hexane gradient. The desired fractions were combined and evaporated to provide the 5-allyl intermediate. This intermediate (580 mg) was subjected to catalytic hydrogenation in ethyl acetate employing 5% palladium on carbon as the catalyst. After the theoretical amount of hydrogen was consumed, the reaction mixture was filtered through a celite mat and evaporated to dryness providing 550 mg of the crude title product. Crystallization from ethyl acetate/hexane provided product with a melting point of 110°-112° C.

Analysis for $C_{19}H_{22}O_4$:
Calc.: C, 72.59; H, 7.05;
Found: C, 72.36; H, 7.17.

EXAMPLE 8

(2,3-Dihydro-4-hydroxy-2-methyl-7-benzofuranyl)(2-hydroxyphenyl)methanone

A. Preparation of (3-allyl-2,4-dimethoxyphenyl)(2-methoxyphenyl)methanone.

Five grams of 1,3-dimethoxy-2-allylbenzene were added to a slurry of 9.16 g of zinc chloride in 80 ml of methylene chloride at 0° C. When the temperature stabilized at 0° C., 4.77 g of 2-methoxybenzoyl chloride were added dropwise. The reaction mixture was allowed to warm to room temperature. After stirring 4 hours, the mixture was poured into a slurry of concentrated hydrochloric acid and ice. The mixture was stirred for 1 hour, additional methylene chloride was added, and the layers were separated. The organic layer was washed 3 times with a sodium bicarbonate solution, dried over sodium sulfate, and evaporated in vacuo. Purification by high pressure liquid chromatography over silica gel eluting with 10% ethyl acetate in hexane provided 2.62 g of the desired subtitle intermediate which was used without further purification.

B. Preparation of (2,3-dihydro-4-hydroxy-2-methyl-5-benzofuranyl)(2-hydroxyphenyl)methanone.

One gram of the allyl intermediate from Example 8A above was heated at reflux for 16 hours with 30 ml of 40% hydrobromic acid and 60 ml of acetic acid. After cooling to 25° C., the mixture was evaporated in vacuo. The residue was purified by preparative thin layer chromatography using 20% ethyl acetate in hexane with 0.05% acetic acid. The appropriate band was isolated, extracted with ethyl acetate, dried over sodium sulfate, and evaporated to dryness providing the desired title product in 10% yield as an oil.

Analysis for $C_{16}H_{14}O_4$:
Calc.: C, 71.10; H, 5.22;
Found: C, 71.25; H, 5.39.

EXAMPLES 9 and 10

Following the procedure of Examples 1–3, the following products were prepared from the appropriate dimethoxybenzene and the corresponding benzoyl chloride.

9. (2-hydroxy-4-methoxy-3-methylphenyl)(2-methoxyphenyl)methanone, 31% yield, m.p. 111°-115° C.

Analysis for $C_{16}H_{16}O_4$:
Calc.: C, 70.58; H, 5.92;
Found: C, 70.91; H, 5.61.

10. (2-Chlorophenyl)(2,4-dihydroxy-3-propylphenyl)methanone, 10% yield, oil.

Analysis for $C_{16}H_{15}ClO_3$:
Calc.: C, 66.09; H, 5.16;
Found: C, 63.15; H, 4.89.

EXAMPLE 11

5-[3-Hydroxy-4-(2-hydroxybenzoyl)-2-propylphenoxy]pentanenitrile

A mixture of 3.6 g of (2,4-dihydroxy-3-propylphenyl)(2-hydroxyphenyl)methanone, 1.4 ml of 5-bromopentane nitrile, 100 mg of sodium iodide, and 9.12 g of potassium carbonate in 50 ml of methyl ethyl ketone was heated to 70° C. for approximately 18 hours. The mixture was cooled and partitioned between diethyl ether and water. The organic layer was separated, dried over magnesium sulfate, and evaporated to dryness. The resulting oil was purified by high pressure liquid chromatography over silica gel eluting with a 5-25% ethyl acetate in hexane gradient. Evaporation of the desired fractions and crystallization from diethyl ether/hexane provided 1.31 g of the title product, m.p. 81°-82° C.

Analysis for $C_{21}H_{23}NO_4$:
Calc.: C, 71.37; H, 6.56; N, 3.96;
Found: C, 71.33; H, 6.57. N, 3.86.

EXAMPLE 12

3-Hydroxy-4-(2-hydroxybenzoyl)-2-propylphenoxy)acetonitrile

The title compound was prepared in 12% yield following the procedure of Example 11 employing the phenol of Example 4 and bromoacetonitrile. The product was an oil.

Analysis for $C_{18}H_{17}NO_4$:
Calc.: C, 69.44; H, 5.50; N, 4.50;
Found: C, 70.10; H, 6.06; N, 3.84.

EXAMPLE 13

6-[3-Hydroxy-4-(2-hydroxybenzoyl)-2-propylphenoxy]hexanenitrile

To a solution of 12.5 g of (2,4-dihydroxy-3-propylphenyl)(2-hydroxyphenyl)methanone in 460 ml of dimethylformamide were added 1.83 g of 60% sodium hydride in oil. The mixture was stirred for one hour under a nitrogen atmosphere. A solution of 4.9 ml of 6-bromohexanenitrile in a small volume of dimethylformamide was added. The reaction was stirred at 60° C. overnight, cooled to 25° C., and poured into a diethyl ether/water mixture. The layers were separated, and the organic layer was washed three times with water, dried over magnesium sulfate, filtered, and evaporated. Purification by high pressure liquid chromatography over silica gel eluting with a 15–35% ethyl acetate/hexane gradient, and evaporation of the desired fractions provided 6.1 g of the desired title product. Crystallization from ethyl acetate/hexane provided material with a melting point of 62°–63° C.

Analysis for $C_{22}H_{25}NO_4$:
Calc.: C, 71.91; H, 6.86; N, 3.81;
Found: C, 71.98; H, 6.83; N, 4.04.

EXAMPLES 14–17

The following compounds were prepared according to the procedure of Example 13 employing the appropriate phenol and the corresponding haloalkanenitrile.

14. 7-[3-Hydroxy-4-(2-hydroxybenzoyl)-2-propylphenoxy]heptanenitrile, 29% yield, m.p. 69°–72° C.
Analysis for $C_{23}H_{27}NO_4$:
Calc.: C, 72.42; H, 7.13; N, 3.67;
Found: C, 72.29; H, 7.16; N, 3.51.

15. 4-[3-Hydroxy-4-(2-hydroxybenzoyl)-2-propylphenoxy]butanenitrile, 25% yield, m.p. 71°–73° C.
Analysis for $C_{20}H_{21}NO_4$:
Calc.: C, 70.78; H, 6.24; N, 4.13;
Found: C, 71.00; H, 6.21; N, 4.29.

16. 9-[3-Hydroxy-4-(2-hydroxybenzoyl)-2-propylphenoxy]nonanenitrile, 27% yield.
Analysis for $C_{25}H_{31}NO_4$:
Calc.: C, 73.32; H, 7.63; N, 3.42;
Found: C, 73.48; H, 7.76; N, 3.12.

17. 4-([3-Hydroxy-4-(2-hydroxybenzoyl)-2-propylphenoxy]methyl)benzonitrile, 13% yield, m.p. 160°–161° C.
Analysis for $C_{24}H_{21}NO_4$:
Calc.: C, 74.40; H, 5.46; N, 3.62;
Found: C, 74.19; H, 5.19; N, 3.59.

EXAMPLE 18

5-[3-Hydroxy-4-(2-methoxybenzoyl)-2-propylphenoxy]pentanenitrile

Five grams of 5-[3-hydroxy-4-(2-hydroxybenzoyl)-2-propylphenoxy]pentanenitrile, 11.7 g of potassium carbonate, and 1.42 ml of dimethyl sulfate in 50 ml of 2-butanone were stirred at reflux for approximately 18 hours. After cooling to 25° C., the mixture was partitioned between ethyl acetate and water. The organic layer was separated, washed with one volume of water and one volume of a saturated sodium chloride solution, dried over magnesium sulfate, filtered, and evaporated to dryness leaving a yellow oil which crystallized on standing. Recrystallization from ethyl acetate/hexane provided 4.38 g of the desired title product, m.p. 85°–86.5° C.

Analysis for $C_{22}H_{25}NO_4$:
Calc.: C, 71.91; H, 6.86; N, 3.81;
Found: C, 71.63; H, 7.13; N, 3.59.

EXAMPLE 19

5-[3-Methoxy-4-(2-methoxybenzoyl)-2-propylphenoxy]pentanenitrile

To a solution of 4.12 g of 5-[3-hydroxy-4-(2-hydroxybenzoyl)-2-propylphenoxy]pentanenitrile in 100 ml of dry dimethylformamide were added 1.17 g of sodium hydride. The reaction mixture was stirred under a nitrogen atmosphere for 1 hour at which time 2.77 ml of dimethyl sulfate were added. The mixture was warmed to 65° C. for 18 hours. After cooling to 25° C., the mixture was partitioned between diethyl ether and water. The organic layer was washed twice with water, dried over magnesium sulfate, filtered, and evaporated in vacuo. Purification of the residue by high pressure liquid chromatography using a 15–30% ethyl acetate in hexane gradient provided 3.74 g of the desired title product as an oil.

Analysis for $C_{23}H_{27}NO_4$:
Calc.: C, 72.42; H, 7.13; N, 3.67;
Found: C, 71.96; H, 7.15; N, 2.65.

EXAMPLE 20

5-(3-Methoxy-4-[1-(2-methoxyphenyl)ethenyl]2-propylphenoxy)pentanenitrile

To a suspension of 0.56 g of methyltriphenylphosphonium bromide in 10 ml of dry tetrahydrofuran were added 0.88 ml of a 1.6 molar n-butyllithium solution in hexane. After stirring for 3 hours under a nitrogen atmosphere, 0.5 g of 5-[3-methoxy-4-(2-methoxybenzoyl)-2-propylphenoxy]pentanenitrile were added in 5 ml of tetrahydrofuran. The reaction was stirred for 40 hours at 25° C. and then at 65° C. for 24 hours. After cooling to room temperature, the reaction mixture was filtered and the filtrate was evaporated to dryness. The residue was purified by preparative thin layer chromatography using a solvent system of 10% ethyl acetate in hexane. The appropriate band was isolated, extracted with ethyl acetate, dried over sodium sulfate, and evaporated in vacuo providing 50 mg of the desired title product as an oil.

Analysis for $C_{24}H_{29}NO_3$:
Calc.: C, 75.96; H, 7.70; N, 3.69;
Found: C, 75.76; H, 7.86; N, 3.47.

EXAMPLE 21

(2-Hydroxyphenyl)[2-hydroxy-3-propyl-4-(1H-tetrazol-5-ylmethoxy)phenyl]methanone A mixture of 2.5 g of 4-([3-hydroxy-4-(2-hydroxybenzoyl)-2-propylphenoxy]methyl)benzonitrile and 7.98 g of tri n-butylstannylazide in 50 ml of tetrahydrofuran were heated at reflux for 3 days. An additional 2.66 g of the azide reagent were added and the reaction was heated at reflux for an additional 4 days. The reaction was cooled and 10 ml of a 10:1 methanol/1N hydrochloric acid mixture were added. After stirring for 1 hour, the mixture was poured into an ethyl acetate/water mixture and the layers were separated. The organic layer was washed once with water and once with a saturated sodium chloride solution, dried over magnesium sulfate, filtered, and evaporated in vacuo. The resulting oil was purified by high pressure liquid chromatography eluting with a 40–75% ethyl acetate in hexane gradient containing 0.5% acetic acid. The appropriate fractions were combined, evaporated, and crystallized from ethyl acetate/hexane to provide 1.72 g of the desired title product, m.p. 186°–187° C.

Analysis for $C_{18}H_{18}N_4O_4$:
Calc.: C, 61.01; H, 5.12; N, 15.81;
Found: C, 61.37; H, 4.95; N, 15.88.

EXAMPLES 22–29

The following compounds were prepared from the corresponding nitrile intermediates according to the procedure of Example 21.

22. (2-Hydroxyphenyl)[2-hydroxy-3-propyl-4([4-(1H-tetrazol-5-yl)phenyl]methoxy)phenyl]methanone, 25% yield, m.p. 147°–150° C.

Analysis for $C_{24}H_{22}N_4O_4$:
Calc.: C, 66.97; H, 5.15; N, 13.02;
Found: C, 66.68; H, 5.13; N, 13.27.

23. (2-Hydroxy-3-propyl-4-[4-(1H-tetrazol-5-yl)butoxy]phenyl)(2-methoxyphenyl)methanone, 56% yield, oil.

Analysis for $C_{22}H_{26}N_4O_4$:
Calc.: C, 64.37; H, 6.38; N, 13.65;
Found: C, 64.25; H, 6.51; N, 13.42.

24. (2-Hydroxyphenyl)[2-hydroxy-3-propyl-4-([5-(1H-tetrazol-5-yl)pentyl]oxy)phenyl]methanone, 11% yield. Proton NMR, infra-red, and mass spectra for the product were consistent with the desired structure.

25. (2-Hydroxyphenyl)[2-hydroxy-3-propyl-4-([6-(1H-tetrazol-5-yl)hexyl]oxy)phenyl]methanone, 92% yield, m.p. 93°–95° C.

Analysis for $C_{23}H_{28}N_4O_4$:
Calc.: C, 65.08; H, 6.65; N, 13.20;
Found: C, 65.27; H, 6.85; N, 13.00.

26. (2-Hydroxyphenyl)(2-hydroxy-3-propyl-4[4-(1H-tetrazol-5-yl)butoxy]phenyl)methanone, 61% yield, m.p. 121°–122.5° C.

Analysis for $C_{21}H_{24}N_4O_4$:
Calc.: C, 63.62; H, 6.10; N, 14.13;
Found: C, 63.87; H, 6.32; N, 14.06.

27. (2-Hydroxyphenyl)(2-hydroxy-3-propyl-4-[3-(1H-tetrazol-5-yl)propoxy]phenyl)methanone, 59% yield, 140°–144° C.

Analysis for $C_{20}H_{22}N_4O_4$:
Calc.: C, 62.82; H, 5.80; N, 14.65;
Found: C, 62.98; H, 5.74; N, 14.55.

28. (2-Hydroxyphenyl)[2-hydroxy-3-propyl-4-([8-(1H-tetrazol-5-yl)octyl]oxy)phenyl]methanone, 42% yield, m.p. 114°–115° C.

Analysis for $C_{25}H_{32}N_4O_4$:
Calc.: C, 66.35; H, 7.13; N, 12.38;
Found: C, 66.57; H, 7.26; N, 12.25.

29. (2-Methoxyphenyl)(2-methoxy-3-propyl-4-[4-(1H-tetrazol-5-yl)butoxy]phenyl)methanone, 45% yield, oil.

Analysis for $C_{23}H_{28}N_4O_4$:
Calc.: C, 65.08; H, 6.65; N, 13.20;
Found: C, 62.69; H, 6.33; N, 11.91.

EXAMPLE 30

5-[3-Hydroxy-4-(2-hydroxybenzoyl)-2-propylphenoxy]pentanoic acid

A solution of 10 g of 5-[3-hydroxy-4-(2-hydroxybenzoyl)-2-propylphenoxy]pentanenitrile and 12.9 g of potassium hydroxide in approximately 250 ml of 10% methanol/water was heated at reflux for 5 days. The solution was cooled to room temperature, acidified with hydrochloric acid. The crude product which precipitated was recovered by filtration and purified by high pressure liquid chromatography over silica gel eluting with a 30–40% ethyl acetate in hexane gradient containing 0.5% acetic acid. The appropriate fractions were combined, evaporated, and recrystallized from diethyl ether/hexane to provide 8.0 g of the desired title carboxylic acid, m.p. 88.5°–91.5° C.

Analysis for $C_{21}H_{24}O_6$:
Calc.: C, 67.73; H, 6.50;
Found: C, 67.53; H, 6.73.

EXAMPLE 31

N,N-Diethyl-5-[3-methoxy-4-(2-methoxybenzoyl)-2-propylphenoxy]pentanamide

Five hundred and ten milligrams of 5-[3-methoxy-4-(2-methoxybenzoyl)-2-propylphenoxy]pentanoic acid were dissolved in 20 ml of diethyl ether. After cooling to 0° C. by means of an external ice bath, 1 ml of thionyl chloride was added. The mixture was stirred overnight at 25° C. and evaporated in vacuo. The residue was dissolved in diethyl ether and a large molar excess of diethylamine was added. A white precipitate quickly formed. After 4 hours of stirring, water was added and the layers were separated. The organic layer was washed twice with water, dried over magnesium sulfate, filtered, and evaporated to dryness. The resulting residue was purified by preparative thin layer chromatography eluting with 30% ethyl acetate in hexane. The appropriate band was isolated, extracted, and evaporated to provide 183 mg of the desired title product as an oil.

Analysis for $C_{27}H_{37}NO_5$:
Calc.: C, 71.18; H, 8.19; N, 3.07;
Found: C, 70.94; H, 7.91; N, 2.97.

EXAMPLES 32 and 33

(2-Hydroxy-4-[4-(2-methyl-2H-tetrazol-5-yl)butoxy]3-propylphenyl)(2-methoxyphenyl)methanone and (2-hydroxy-4-4-(1-methyl-1H-tetrazol-5-yl)butoxy]-3-propylphenyl)(2-methoxyphenyl)methanone To a solution of 570 mg of (2-hydroxy-3-propyl-4-[4-(1H-tetrazol-5-yl)butoxy]phenyl)(2-methoxyphenyl)methanone in 40 ml of 2-butanone were added 0.13 ml of dimethyl sulfate and 768 mg of potassium carbonate. After heating at reflux overnight, the mixture was cooled to 25° C. and partitioned between ethyl acetate and water. The organic layer was washed twice with water and once with a saturated sodium chloride solution. After drying over magnesium sulfate, filtration, and evaporation, the residue was purified by preparative thin layer chromatography eluting with 50% ethyl acetate in hexane. The more mobile material was identified as the 1-methyltetrazolyl isomer whereas the less mobile product was identified as the 2-methyl isomer.

32. (2-Hydroxy-4-[4-(2-methyl-2H-tetrazol-5yl)butoxy]-3-propylphenyl)(2-methoxyphenyl)methanone, 137 mg, oil.

Analysis for $C_{23}H_{28}N_4O_4$:
Calc.: C, 65.08; H, 6.65; N, 13.20;
Found: C, 60.99; H, 6.90; N, 10.09.

33. (2-Hydroxy-4-[4-(1-methyl-1H-tetrazol-5-yl)butoxy]3-propylphenyl)(2-methoxyphenyl)methanone, 86 mg, oil.

Analysis for $C_{23}H_{28}N_4O_4$:
Calc.: C, 65.08; H, 6.65; N, 13.20;
Found: C, 64.96; H, 6.41; N, 12.92.

The compounds of formula I inhibit the enzymes 5-lipoxygenase and fatty acid cyclooxygenase. The compounds are therefore useful as anti-inflammatory, anti-allergy and anti-asthma agents. These pharmacodynamic effects of the compounds of this invention were demonstrated in the following test systems.

5-Lipoxygenase (5-LPO) Assay

Ten milliliters of a 2% casein solution were injected intraperitoneally into guinea pigs weighing 250–300 gm. After 16–18 hours, the guinea pigs were killed by suffocation in a carbon dioxide chamber. The peritoneal cavity was infused with 70 ml of saline and 40–50 ml of the fluid were recovered from the cavity. After centrifugation, cell pellets were washed twice in Hank's balanced salt solution (HBSS) without calcium ion.

The cells were then suspended in 5 ml of sodium phosphate buffer, pH 7.1 containing 1 mM EDTA, and 0.1% gelatin. About $20-30 \times 10^7$ cells were obtained from one guinea pig. Analysis for the cell composition indicated that more than 95 percent of the cells were polymorphonuclear leukocyte (PMNL).

The PMNL suspension was disrupted by five ½ second pulse sonications at the setting of 3 in a Branson Sonifier, Model 350, equipped with a microtip. The sonicates were combined and centrifuged at $30,000 \times g$ for 10 minutes. The supernatant was kept frozen at $-70°$ C. until use.

Enzyme activity was determined by assaying for 5-HETE formation by first incubating 0.2 ml of the supernatant obtained from the PMNL sonicate with the test compound, 1 mM $CaCl_2$, 2 mM ATP, and 1 mM GSH for 5 minutes at 37° C. The mixture is treated with 5 $\mu$M $^{14}C$-arachidonic acid and incubated at 37° C. an additional 10 minutes. The enzyme reaction was then stopped by the addition of 10 $\mu$l of 1M citric acid and 10$\mu$l of an alcohol solution containing 20 mg/ml each of indomethacin and butylated hydroxyanisole (BHA). The reaction mixture was spotted (50 $\mu$l on a silica gel plate (Baker TLC plate S1250-PA-19C) and subjected to TLC in a solvent system of ethyl acetate/2,2,4-trimethylpentane/glacial acetic acid/water (90:50:20:100).

The radioactivity of the arachidonic acid and its metabolites (5-HETE and LTB$_4$) was visualized from a developed x-ray film which had been exposed to the TLC plate 1–2 days. The amount of 5-HETE formed was quantitated by scraping the silica gel area corresponding to the spot on the x-ray film, and the radioactivity determined in a Isocap/300 liquid scintillation counter (Searle Analytic, Inc.).

The percent inhibition of the formation of 5-HETE was determined for each concentration of test compound tested as compared to a control experiment wherein no test compound was added. The concentration and percent inhibition values were plotted on semi log paper and the concentration in which formation of 5-HETE is inhibited by 50% ($IC_{50}$) was determined by interpolation. The results are summarized in Table I.

Fatty Acid Cyclooxygenase (FCO) Assay

Microsomes were prepared from 185 bags of human platelets (each bag containing the platelets from one pint of blood prepared using differential centrifugation procedures). The platelets from approximately 60 bags were prepared at one time. Platelet-rich plasma (500 g) was centrifuged at $10,000 \times g$ for 20 minutes, and the platelet pellet was suspended in 100 ml of 0.1M potassium phosphate buffer, pH 8.0, with a Teflon glass homogenizer and sonicated for 5.0 minutes with a Bronson Sonifier (Model 350) in a rosette flask cooled in ice water. Disrupted platelets were centrifuged 15 minutes at $10,000 \times g$. The supernatant was centrifuged at $100,000 \times g$ for 90 minutes and the microsomal pellets were homogenized in 25 ml of 20% sucrose containing 1.0% Triton X-100 detergent. After 30 minutes at 4° C., the solubilized microsomes were centrifuged at $100,000 \times g$ for 60 minutes. The yellow supernatant was removed and stored at $-70°$ C.

The solubilized fatty acid cyclooxygenase was applied to a 440 ml electrofocusing column (LKB-8012) containing 1% phisolytes (Brinkman Instruments, Westburgh, NY), pH 2–11, with the cathode at the top of the column. The enzyme was layered onto the column at the appropriate time so that its sucrose concentration was equal to that of the column gradient. This was accomplished by checking the gradient concentration periodically with a sucrose hand refractometer. Electrofocusing was carried out for 16 hours with an initial voltage of 400 V and a final voltage of 900–1,000 volts. Fractions were collected (20 ml) and assayed for PGE$_2$ formation. Active peak fractions were pooled and concentrated by ultrafiltration (XM 100A) to a volume of 3–5 ml.

Active fractions from electrofocusing were applied to a G-200 Sephadex column (2 cm $\times$ 46 cm) and eluted with 10 mM potassium phosphate buffer, pH 7.0, in 5 ml fractions. After assay, active fractions were poored and concentrated to 1.0 ml by ultrafiltration (XM 100A), and kept frozen at $-70°$ C.

Enzyme activity was determined by assaying for PGE$_2$ formation by preincubating the enzyme with 10 mmol/l imidazole phosphate buffer, pH 8.0, 2 mmol/l epinephrine, 2 mmol/l methemoglobin, and the test compound (30 $\mu$g/ml) in a total volume of 0.2 ml for one minute at 37° C. After preincubation, 5 mmol/l $^{14}C$-arachidonic acid were added and the mixture was incubated an additional 0.5 minutes at 37° C. The enzyme reaction was stopped by the addition of 2 $\mu$l of indomethacin (2 mg/ml) in alcohol.

The reaction mixture was spotted (50 μl) on a silica gel (LQ6D) plate and subjected to TLC. The solvent system consisted of chloroform-methanol-glacial acetic acid (90:5:5, v/v/v) and the relative mobilities were $PGF_{2\alpha}=0.235$, and $PGE_2=0.47$. The silica gel on the plate was scraped in 1 cm sections, suspended in 5 ml of the scintillation fluid [5.88 g of 2,5-diphenyloxazole and 118 mg of 1,4-bis(5-phenyloxazol-2-yl)benzene] dissolved in 650 ml of toluene and 350 ml of Triton X-100 and the radioactivity was determined in an Isocap/300 liquid scintillation counter (Searle Analytic, Inc., Southfield, Mich.). Another 50 μl of the mixture was added to 10 ml of the Triton X-100 based scintillation fluid, and the radioactivity was determined so that the amount of radioactivity recovery from the TLC plate could be ascertained. $PGE_2$ formation for each test compound was determined as a percent of control experiments wherein no test compound was added. Data is expressed in Table I either as the percent inhibition of formation of $PGE_2$ at a test compound concentration of 30 μg/ml, or as an $IC_{50}$ for inhibition of $PGE_2$ formation.

TABLE I

| Compound of Example No. | $IC_{50}$ (μg/ml) FCO | 5-LPO |
| --- | --- | --- |
| 1 | 5.5 | 0.3 |
| 2 | 2.8 | 0.8 |
| 3 | 1.4 | 0.3 |
| 4 | 0.3 | 1.6 |
| 6 | 12%** | 4 |
| 7 | 5.5 | 20 |
| 8 | NT* | 8 |
| 9 | 35%** | 1 |
| 10 | 100%** | 5 |
| 11 | 30 | 1 |
| 12 | 10 | 7 |
| 13 | 40%** | 2 |
| 14 | 37%** | 0.2 |
| 17 | 48%** | 94%** |
| 18 | 15%** | 8 |
| 19 | 9%** | 10 |
| 20 | NT | 30 |
| 21 | 0%** | 0%** |
| 22 | 14 | 4.0 |
| 23 | 17%** | 0.7 |
| 24 | NT | 12 |
| 25 | 5.4 | 5 |
| 26 | 44%** | 0.5 |
| 27 | 15%** | 4.0 |
| 28 | 5.5 | 0.6 |
| 29 | <5%** | 6 |
| 30 | 45 | 37%*** |
| 31 | <5%** | 8 |
| 32 | 10% | 0.2 |
| 33 | 0%** | 0.3 |

*not tested
**percent inhibition at 30 μg/ml.
***percent inhibition at 10 μg/ml.

The compounds of Formula I have also been found to be active in an in vivo experimental arthritis model as demonstrated by the following test system.

Collagen-Induced Arthritis Assay

Type II collagen was isolated from bovine articular cartilage by the method of Strawich and Nimni Biochemistry, 10, 3905 (1971)]. The collagen was dissolved in 0.1 M acetic acid and stored at −20° C. Type II collagen solution was diluted to 2 mg/ml concentration and emulsified thoroughly with an equal volume of incomplete Freund's adjuvant (ICFA). The emulsion containing approximately 0.5 mg of collagen was injected intradermally on day 0 to groups of 6 inbred Lewis male rats (Charles River Breeders; 170–200 g) at various sites in the dorsal area. The hindpaw volumes of each rat were measured and recorded three times a week throughout the test period to assess the inflammatory reaction. The test group animals received compounds under test as suspensions in carboxymethylcellulose vehicle, by oral gavage, 5 days per week (Monday–Friday), beginning on day 1. Control animals received vehicle without a test compound. At the end of the test (day 28 or 30), the blood of these animals was drawn by cardiac puncture and the serum anti-type II collagen antibody levels were estimated by passive hemagglutination technique, using glutaraldehyde treated sheep red cells, to which type II collagen is conjugated [Avramaes et al., Immunochemistry, 6, 67 (1969); Andriopoulos et al., Arth. Rheum. 19, 613 (1976)]. The cellular response or delayed-type hypersensitivity response to type II collagen was measured by the radiometric ear index assay [Kostiala, Immunology, 33, 561 (1977)]. In certain experiments, the bone damage occurring because of immunization with type II collagen and the effects of drugs were determined from the radiographs of the hindpaws of two or three representative animals from each group. Injections of ICFA without collagen II were employed in some rats as a negative control; these rate received only carbomethoxycellulose vehicle during the test.

The results of testing the compounds of Formula II in the collagen-induced arthritis system are summarized in Table II. The % inhibition was calculated according to the following formula:

$$\% \text{ inhibition} = \left[1 - \frac{Vt - Vv}{Vc - Vv}\right] \times 100$$

where Vt is the hindpaw volume of a compound-treated animal (test group), Vc is the hindpaw volume of a non-compound-treated animal (carbomethoxycellulose vehicle only—the control group), and Vv is the hindpaw volume of a vehicle (carbomethoxycellulose) treated animal which received ICFA with no collagen II (negative control group).

TABLE II

| Inhibition of Collagen-Induced Arthritis | | |
| --- | --- | --- |
| Compound of Example No. | Dose mg/kg* | % inhibition* |
| 4 | 50 | 47% |
| 9 | 50 | 0% |
| 11 | 25 | 31% |
|  | 10 | 0% |
| 23** | 25 | 69% |
|  | 10 | 67% |
|  | 10 | 65% |
|  | 3 | 33% |
| 25** | 25 | 39% |
|  | 10 | 69% |
|  | 10 | 0% |
| 26 | 50 | 67% |
|  | 50 | 49% |
| 26** | 50 | 100% |
|  | 50 | 95% |
|  | 30 | 62% |

TABLE II-continued

Inhibition of Collagen-Induced Arthritis

| Compound of Example No. | Dose mg/kg* | % inhibition* |
|---|---|---|
|  | 25 | 71% |
|  | 10 | 3% |
|  | 10 | 65% |
|  | 3 | 65% |
| 28** | 30 | 95% |
|  | 10 | 48% |
|  | 3 | 65% |
| 30 | 50 | 24% |

*See text for experimental method.
**Sodium salt.

The compounds of Formula I are antiinflammatory and antiarthritic agents and this invention provides such methods. The methods comprise administering a compound of Formula I by various routes including the oral, rectal, transdermal, subcutaneous, intravenous, intramuscular, or intranasal routes, being usually employed in the form of a pharmaceutical composition. It is a special feature of these compounds that they are effective following oral administration. Such compositions are prepared in a manner well known in the pharmaceutical art and comprise at least one active compound. Accordingly, the invention also includes pharmaceutical compositions comprising as active ingredient a compound of Formula I associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl-and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The active compounds are effective over a wide dosage range. For example, dosages per day will normally fall within the range of about 0.5 to about 200 mg/kg of body weight. In the treatment of adult humans, the range of about 1 to about 50 mg/kg, in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following formulation examples may employ as active compounds any of the compounds of Formula I. The examples are illustrative only and are not intended to limit the scope of the invention in any way.

EXAMPLE 34

Hard gelatin capsules are prepared using the following ingredients:

|  | Quantity (mg/capsule) |
|---|---|
| (2-hydroxy-3-propyl-4-[4-(1H—tetrazol-5-yl)butoxy]phenyl)(2-methoxyphenyl)methanone, sodium salt | 250 |
| Starch dried | 200 |
| Magnesium stearate | 10 |

The above ingredients are mixed and filled into hard gelatin capsules in 460 mg quantities.

EXAMPLE 35

A tablet formula is prepared using the ingredients below:

|  | Quantity (mg/tablet) |
|---|---|
| (2-methoxyphenyl)(2-hydroxy-3-propyl-4-[4-(1H—tetrazol-5-yl)butoxy]phenyl)-methanone, potassium salt | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 36

An aerosol solution is prepared containing the following components:

|  | Weight % |
|---|---|
| (2,4-dihydroxy-3-propylphenyl)-(2-hydroxyphenyl)methanone | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 37

Tablets each containing 60 mg of active ingredient are made up as follows:

| | |
|---|---|
| (2-hydroxyphenyl)(2-hydroxy-3-propyl-4-[4-(1H—tetrazol-5-yl)butoxy]phenyl)methanone | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 38

Capsules each containing 80 mg of medicament are made as follows:

| | |
|---|---|
| 5-[3-hydroxy-4-(2-hydroxybenzoyl)-2-propylphenoxy]pentanoic acid | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 39

Suppositories each containing 225 mg of active ingredient are made as follows:

| | |
|---|---|
| f-([3-hydroxy-4-(2-hydroxybenzoyl)-2-propylphenoxy]methyl)benzonitrile | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 40

Suspensions each containing 50 mg of medicament per 5 ml dose are made as follows:

| | |
|---|---|
| 5-[3-methoxy-4-(2-methoxybenzoyl)-2-propylphenoxy]pentanamide | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 41

Capsules each containing 150 mg of medicament are made as follows:

| | |
|---|---|
| (2,4-dimethoxy-3-propylphenyl)(2-methoxyphenyl)methanone | 150 mg |
| Starch | 164 mg |
| Microcrystalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.

I claim:

1. A compound of the formula

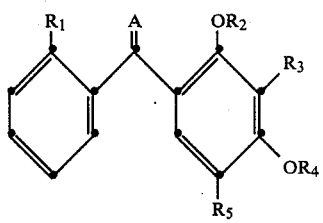

and pharmaceutically acceptable salts thereof wherein
$R_1$ is —OH, —O—($C_1$–$C_4$ alkyl), halo, or —OCO($C_1$–$C_4$ alkyl);
A is O;
$R_2$ is hydrogen or $C_1$–$C_4$ alkyl;
$R_3$ is $C_1$–$C_4$ alkyl or $C_2$–$C_4$ alkenyl;
$R_4$ is —H, $C_1$–$C_4$ alkyl, —CO($C_1$–$C_4$ alkyl), -alk-$R_6$, or

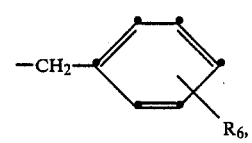

$R_5$ is —H or $C_1$–$C_4$ alkyl; and $R_6$ is —CN, —COOH, —COO($C_1$–$C_4$ alkyl), —CONR$_7$R$_8$, or

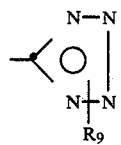

where $R_7$ and $R_8$ are each indenpendently hydrogen or $C_1$–$C_3$ alkyl, $R_9$ is hydrogen or $C_1$–$C_4$ alkyl, and "alk" is a $C_1$–$C_8$ alkylene radical.

2. A compound of claim 1 wherein $R_3$ is propyl.

3. A Compound of claim 2 wherein $R_4$ is

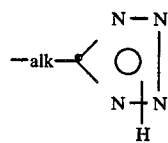

4. The compound of claim 3 which is (2-hydroxy-3-propyl-4-[4-(1H-tetrazol-5-yl)butoxy]phenyl)-(2-methoxyphenyl)methanone or a pharmaceutically acceptable base addition salt thereof.

5. The compound of claim 3 which is (2-hydroxyphenyl)(2-hydroxy-3propyl-4[4-(4H-tetrazol-5yl)butoxy]phenyl)methanone or a pharmaceutically acceptable base addition salt thereof.

6. The compound of claim 3 which is (2-methoxyphenyl)(2-methoxy-3propyl-4-[4-(1H-tetrazol-5yl)-butoxy]phenyl)methanone or a pharmaceutically acceptable base addition salt thereof.

7. A method of treating inflammation in mammals which comprises administering to said mammal an effective amount of a compound of claim 1.

8. The method of claim 7 employing a compound wherein $R_3$ is propyl.

9. The method of claim 8 employing a compound wherein $R_4$ is

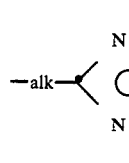

10. The method of claim 9 employing the compound (2-hydroxy-3-propyl-4[4-(1H-tetrazol-5-yl)butoxyl]-phenyl)(22-methoxyphenyl)methanone or a pharmaceutically acceptable base addition salt thereof.

11. The method of claim 9 employing the compound (2-hydroxyphenyl)(2-hydroxy-3-propyl-4-[4-(1H-tetrazol-5-yl)butoxy]phenyl)methanone or a pharmaceutically acceptable base addition salt thereof.

12. The method of claim 9 employing the compound (2-methoxyphenyl)(2-methoxy-3-propyl-4-[4-1H-tetrazol-5-yl)butoxy]phenyl)methanone or a pharmaceutically acceptable base addition salt thereof.

13. A pharmaceutical formulation comprising a compound of claim 1 in association with a pharmaceutically acceptable carrier, diluent, or excipient therefor.

14. A formulation according to claim 13 employing a compound wherein $R_3$ is propyl.

15. A formulation according to claim 14 employing a compound wherein $R_4$ is

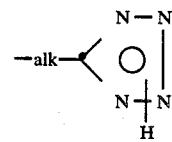

16. A formulation according to claim 15 employing the compound (2-hydroxy-3-propyl-4-[4-(1H-tetrazol-5-yl)butoxy]phenyl)(2-methoxyphenyl)methanone or a pharmaceutically acceptable base addition salt thereof.

17. A formulation according to claim 15 employing the compound (2-hydroxyphenyl)(2-hydroxy-3-propyl-4-[4-(1H-tetrazol-5-yl)butoxy]phenyl)methanone or a pharmaceutically acceptable base addition salt thereof.

18. A formulation according to claim 15 employing the compound (2-methoxyphenyl)(2-methoxy-3-propyl-4-[4-(1H-tetrazol-5-yl)butoxy]phenyl)methanone or a pharmaceutically acceptable base addition salt thereof.

* * * * *

UNITED STATES PATENT AND TRADEMARK OFFICE
CERTIFICATE OF CORRECTION

PATENT NO. : 4,801,616

DATED : January 31, 1989

INVENTOR(S) : D. Mark Gapinski

It is certified that error appears in the above-identified patent and that said Letters Patent is hereby corrected as shown below:

Column 23, line 13, "indenpendently" should read --independently--

Column 23, line 14, "$C_{1-c3}$" should read --$C_1$-$C_3$--.

Column 23, line 35, "phenyl)(2-hydroxy-3propyl-4-[4-(4H-tetrazol-5yl)butox-" should read
--phenyl)(2-hydroxy-3-propyl-4-[4-(1H-tetrazol-5-yl)butox- --.

Column 24, line 11, "phenyl)(22-methoxyphenyl)methanone" should read -- phenyl)(2-methoxyphenyl)methanone --.

Signed and Sealed this

Twenty-fourth Day of October, 1989

Attest:

DONALD J. QUIGG

Attesting Officer

Commissioner of Patents and Trademarks